US008731512B2

(12) United States Patent
Borras et al.

(10) Patent No.: US 8,731,512 B2
(45) Date of Patent: May 20, 2014

(54) SYSTEM AND METHOD FOR EFFECTING CONTEXT-COGNIZANT MEDICAL REMINDERS FOR A PATIENT

(75) Inventors: Jaime Borras, Miramar, FL (US); Don Rosen, Staten Island, NY (US); Jeffrey A. Wolf, Miami Beach, FL (US)

(73) Assignee: Generationone, Miami Beach, FL (US)

( * ) Notice: Subject to any disclaimer, the term of this patent is extended or adjusted under 35 U.S.C. 154(b) by 579 days.

(21) Appl. No.: 12/885,522

(22) Filed: Sep. 19, 2010

(65) Prior Publication Data

US 2011/0070835 A1 Mar. 24, 2011

Related U.S. Application Data

(60) Provisional application No. 61/244,414, filed on Sep. 21, 2009.

(51) Int. Cl.
*H04M 11/04* (2006.01)
(52) U.S. Cl.
USPC .......... 455/404.1; 455/404.2; 455/414.1; 455/414.3; 455/456.1; 455/456.5; 455/456.6; 455/41.1; 455/41.2; 455/517; 455/521; 455/556.1; 455/556.2; 340/539.1; 340/539.12; 340/539.13; 340/539.14; 340/539.15; 340/539.16; 340/539.17; 340/539.18; 340/539.22; 340/539.24; 340/539.25; 340/539.26; 607/60
(58) Field of Classification Search
USPC ............ 455/404.1–404.2, 414.1–414.3, 455/456.1–456.6, 457, 41.1–41.2, 455/556.1–556.2, 517, 521; 340/539.1, 340/539.11–539.19, 539.2, 539.21–539.29; 607/60, 62, 63
See application file for complete search history.

(56) References Cited

U.S. PATENT DOCUMENTS

| 6,263,280 | B1 * | 7/2001 | Stingone, Jr. | 701/485 |
|---|---|---|---|---|
| 6,544,171 | B2 * | 4/2003 | Beetz et al. | 600/300 |
| 6,792,396 | B2 * | 9/2004 | Inda et al. | 702/188 |
| 6,847,892 | B2 * | 1/2005 | Zhou et al. | 701/408 |
| 7,825,794 | B2 * | 11/2010 | Janetis et al. | 340/539.13 |
| 7,978,063 | B2 * | 7/2011 | Baldus et al. | 340/539.12 |
| 8,112,293 | B2 * | 2/2012 | Howell et al. | 705/3 |
| 8,300,560 | B2 * | 10/2012 | Nowlan et al. | 370/270 |
| 2001/0026240 | A1 * | 10/2001 | Neher | 342/357.07 |
| 2003/0125017 | A1 * | 7/2003 | Greene et al. | 455/414 |
| 2004/0162035 | A1 * | 8/2004 | Petersen et al. | 455/90.1 |

* cited by examiner

*Primary Examiner* — Tuan A Tran
(74) *Attorney, Agent, or Firm* — Bradley Arant Boult Cummings LLP

(57) ABSTRACT

A system for effecting context-cognizant medical reminders for a patient; the system including: (a) at least one sensor unit situated proximately with the patient; the at least one sensor unit sensing and indicating at least one aspect of a personal context of the patient; (b) at least one long-range communication unit configured for wireless communication with a remote patient care monitoring facility via a wireless communication network; and (c) at least one short-range communication unit communicatingly coupled with the at least one sensor unit and with the at least one long-range communication unit; the at least one short-range communication unit and the at least one long-range communication unit cooperating to convey information from the at least one sensor unit to the remote patient care monitoring facility regarding the personal context of the patient.

3 Claims, 10 Drawing Sheets

US 8,731,512 B2

SYSTEM AND METHOD FOR EFFECTING CONTEXT-COGNIZANT MEDICAL REMINDERS FOR A PATIENT

This application claims benefit of prior filed Provisional Patent Application Ser. No. 61/244,414, filed Sep. 21, 2009.

BACKGROUND OF THE INVENTION

The present invention is directed to medical patient monitoring, and especially to effecting patient monitoring in a manner cognizant of the extant environment or surroundings of the patient being monitored.

Patients may receive reminders relating to taking medication or performing medical tests at various times during a day. The timing of the reminders may be predetermined and may, therefore, be provided to the patient at an inopportune time or when the reminder is no longer necessary.

Prior art systems for effecting reminders for medical procedures for patients have heretofore been dispatched to a patient at pre-programmed times and dates independent of any changes or circumstances experienced by the patient. If an event was canceled or rescheduled or if another change occurred in the environment or circumstances of a patient, the schedule for reminders for that patient would have to be manually reprogrammed.

It has been observed that preprogrammed reminders may eventually become monotonous and may be ignored by a patient. Further, preselected times for reminders may interfere with a patient's activities, which activities may change from day to day. By way of example and not by way of limitation, if a reminder is scheduled during a patient's working hours, inadvertently or otherwise, or if the patient has a sudden change of routine or schedule away from home, taking vital signs or taking medication may be very inconvenient. Taking vital signs such as, for example, blood sugar, blood pressure, weight, lung capacity or another test for monitoring a possible chronic disease may be inconvenient away from home. Ill-timed reminders sent according to a prior art preprogrammed schedule to carry out such monitoring may be ignored by a patient when they are received, and may be later forgotten altogether.

By way of further example and not by way of limitation, a diabetic patient may initially monitor blood sugar four times per day at the beginning of a treatment program. As time passes with proper medication, diet and other care, the parent's glucose may stabilize and monitoring of blood sugar may be reduced to three times per day. The present invention permits such an adjustment to be based upon observed test results without having to manually reprogram the reminder schedule.

By way of still further example and not by way of imitation, if a patient has taken a vital sign reading just prior to a reminder being scheduled to be sent, then a reminder would be a bother. The present invention permits automatic noting that the vital sign has been taken and reminder for that vital sign may be withheld.

It would be useful to provide a system and method for scheduling the sending of medical reminders to a patient that may be cognizant of the context, surroundings or environment in which the patient is operating when determining what reminders to send to the patient or determining whether to send a reminder to the patient.

There is a need for a system and method for effecting context-cognizant (i.e., aware of a patient's environment or circumstances) medical reminders for a patient that permits rescheduling or reprogramming timing of reminders when a patient's environment or conditions change.

SUMMARY OF THE INVENTION

A system for effecting context-cognizant medical reminders for a patient; the system including: (a) at least one sensor unit situated proximately with the patient; the at least one sensor unit sensing and indicating at least one aspect of a personal context of the patient; (b) at least one long-range communication unit configured for wireless communication with a remote patient care monitoring facility via a wireless communication network; and (c) at least one short-range communication unit communicatingly coupled with the at least one sensor unit and with the at least one long-range communication unit; the at least one short-range communication unit and the at least one long-range communication unit cooperating to convey information from the at least one sensor unit to the remote patient care monitoring facility regarding the personal context of the patient.

A method for effecting context-cognizant medical reminders for a patient; the system including: (a) providing at least one sensor unit situated proximately with the patient; the at least one sensor unit sensing and indicating at least one aspect of a personal context of the patient; (b) providing at least one long-range communication unit configured for wireless communication with a remote patient care monitoring facility via a wireless communication network; (c) providing at least one short-range communication unit communicatingly coupled with the at least one sensor unit and with the at least one long-range communication unit; and (d) operating the at least one short-range communication unit and the at least one long-range communication unit cooperatively to convey information from the at least one sensor unit to the remote patient care monitoring facility regarding the personal context of the patient.

It is, therefore, a feature of the present invention to provide a system and method for effecting context-cognizant medical reminders for a patient that permits rescheduling or reprogramming timing of reminders when a patient's environment or conditions change.

Further features of the present invention will be apparent from the following specification and claims when considered in connection with the accompanying drawings, in which like elements are labeled using like reference numerals in the various figures, illustrating the preferred embodiments of the invention.

DETAILED DESCRIPTION OF THE PREFERRED EMBODIMENT

Figure 1:
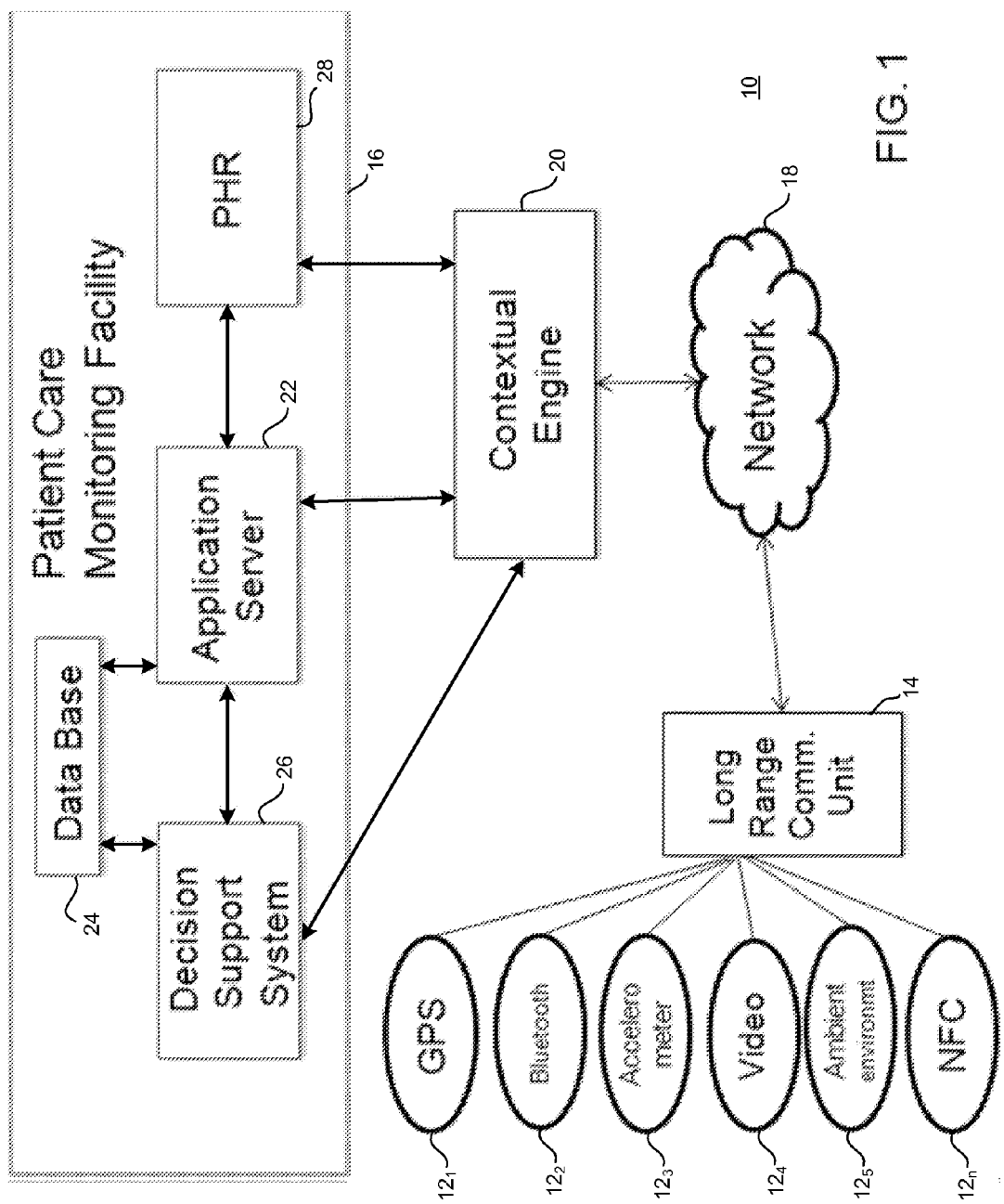
FIG. 1 is a schematic diagram of a system for effecting context-cognizant reminders for a patient.

The terms "coupled" and "connected", along with their derivatives, may be used herein. It should be understood that these terms are not intended as synonyms for each other. Rather, in particular embodiments, "connected" may be used to indicate that two or more elements are in direct physical or electrical contact with each other. "Coupled" may be used to indicated that two or more elements are in either direct or indirect (with other intervening elements between them) physical or electrical contact with each other, or that the two or more elements co-operate or interact with each other (e.g. as in a cause and effect relationship).

As used herein, the term "exemplary" indicates an example and not necessarily an ideal.

Context Reminders

Context reminders may also be referred to as smart reminders. Context reminders recognize a patient's behavioral patterns and optimize a reminder's alerting efficacy. A context reminder relies on surrounding data that is collected by a patient's intelligent wireless communication unit, such as by way of example and not by way of limitation, a smart phone or other smart device (such as a pendant). The collected information is preferably processed and analyzed in conjunction with the patient's Personal Health Record (PHR) and an Application Server which contains pre-programmed reminders for the patient.

smart devices utilize sensors that can, by way of example and not by way of limitation, monitor a patient's location via GPS (Global Positioning System), capture biomedical vital signs from medical accessories via wireless connections like Bluetooth, detect via accelerometers whether a patient is at rest or moving, determine if a patient is talking on the phone or sending text or browsing the internet, and process and analyze what is around a patient via listening to the environment or via monitoring a video feed.

Contextual data (also referred to herein as environmental or surrounding data) collected by a smart device may be compared with a patient's PHR information and a pre-programmed schedule of reminders in the Application server. The schedule of reminders may be altered based on the rules from a contextual engine. For example, if the contextual engine determines that the user has already taken particular vital signs or medication within an acceptable time frame then a pre-scheduled reminder associated with that vital sign or medication may not be sent.

By way of further example and not by way of limitation, if a patient is driving at the time of a scheduled reminder, then the reminder schedule may be altered to wait for an acceptable time frame until the patient gets home. Alternatively, if received GPS data indicates that the patient is driving away from home, a different reminder may be sent.

The schedule and the content of reminders may be based on a patient's location and activities.

In yet another example, if the contextual engine identifies that a patient has a high compliance ratio (i.e., number of reminders answered versus sent) and the biometric data monitored and received is well within limits, then the system may send a query to a case manager asking for approval to reduce the number of reminders from four times a day to three, and then to two times a day. Alternatively, instead of sending a reminder daily to send the reminder every other day.

The contextual engine may analyze the conditions around the patient (i.e., the patient's context, circumstances or environment) when a reminder is not answered and change the reminder accordingly to improve engagement. For example, if a scheduled reminder is sent during a patient's working hours, the contextual engine may recommend sending the reminder at a different time. A report with the reasoning for changing a reminder schedule may be sent to a case manager for final approval. The case manager may be located at a remote patient monitoring facility. Thus a feedback loop may be established to improve a patient's engagement and compliance.

Contextual Reminders may also enable new programs like a Personal Health Coach (PHC) which is based on the PHR content and patient's consent. A PHC may provide guidance towards improving a patient's health. For example, if a patient's Body Mass Index (BMI) is above average, the PHC can monitor the patient's activity by monitoring an accelerometer output (e.g., a pedometer) and provide reminders if not enough activity or exercise is recorded. Obesity is a leading cause of chronic illness. The PHC can also provide suggestions to a patient base on the patient's record and the places that the patient visits for food intake. By way of example and not by way of imitation, at the grocery store a PHC may provide suggestions regarding what to purchase so as to have balanced meals for the week, or if the PHC detects entering a particular restaurant, reminders for a balanced diet may be provided.

Other examples of contextual reminders may include: prescription refill reminders based on feedback from a smart pill box, doctor's office visit recommendations based on biometric data content and time of last doctor visit, fall alerts if a smart device detects the lack of stability in a patient's walk and incentive programs to encourage "good health habits" by a patient.

FIG. 1 is a schematic diagram of a system for effecting context-cognizant reminders for a patient. In FIG. 1, a reminder system 10 includes a plurality of sensor units including a Global Positioning System position determining unit $12_1$, a Bluetooth or similar wireless linking unit $12_2$, an accelerometer unit $12_3$, a video unit $12_4$, an ambient environment measuring unit $12_5$ and a Near Field Communication (NFC) unit $12_n$.

The indicator "n" is employed to signify that there can be any number of sensor units in reminder system 10. The inclusion of six sensor units $12_1$, $12_2$, $12_3$, $12_4$, $12_5$ $12_n$ in FIG. 1 is illustrative only and does not constitute any limitation regarding the number of sensor units that may be included in the reminder system of the present invention. Throughout this description, use of a reference numeral using a generic subscript herein may be taken to mean that any respective member of the plurality of elements having the same reference numeral may be regarded as included in the description. Thus, by way of example and not by way of limitation, referring to sensor unit $12_n$ in describing FIG. 1 may be taken to mean that any sensor unit—Global Positioning System position determining unit $12_1$, Bluetooth or similar wireless linking unit $12_2$, accelerometer unit $12_3$, video unit $12_4$, ambient environment measuring unit $12_5$ or Near Field Communication (NFC) unit $12_n$. (FIG. 1) or another sensor unit not illustrated but understood by those skilled in the art of biometric measurement sensor devices—may be regarded as capable of employment as described.

Reminder system 10 also includes a long-range communication unit 14. Long-range communication unit 14 may be embodied in an intelligent wireless communication unit, such as by way of example and not by way of limitation, a smart phone or other smart device (such as a pendant). Long-range communication unit 14 is configured for wireless communication with a remote patient care monitoring facility 16 via a network 18.

Patient care monitoring facility 16 may include an application server 22 coupled with a database 24, with a decision support system 26 and with a Patient Health Record (PHR) 28. Preferably database 24 is also coupled with decision support system 26.

A contextual engine 20 may be coupled with patient care monitoring facility 16. Specifically, contextual engine 20 may be coupled with decision support system 26, application server 22 and PHR 28. Contextual engine 20, decision support system 26, application server 22 and PHR 28 may cooperate, with support from database 24, to interpret information provided by sensors $12_n$.

Figure 2:
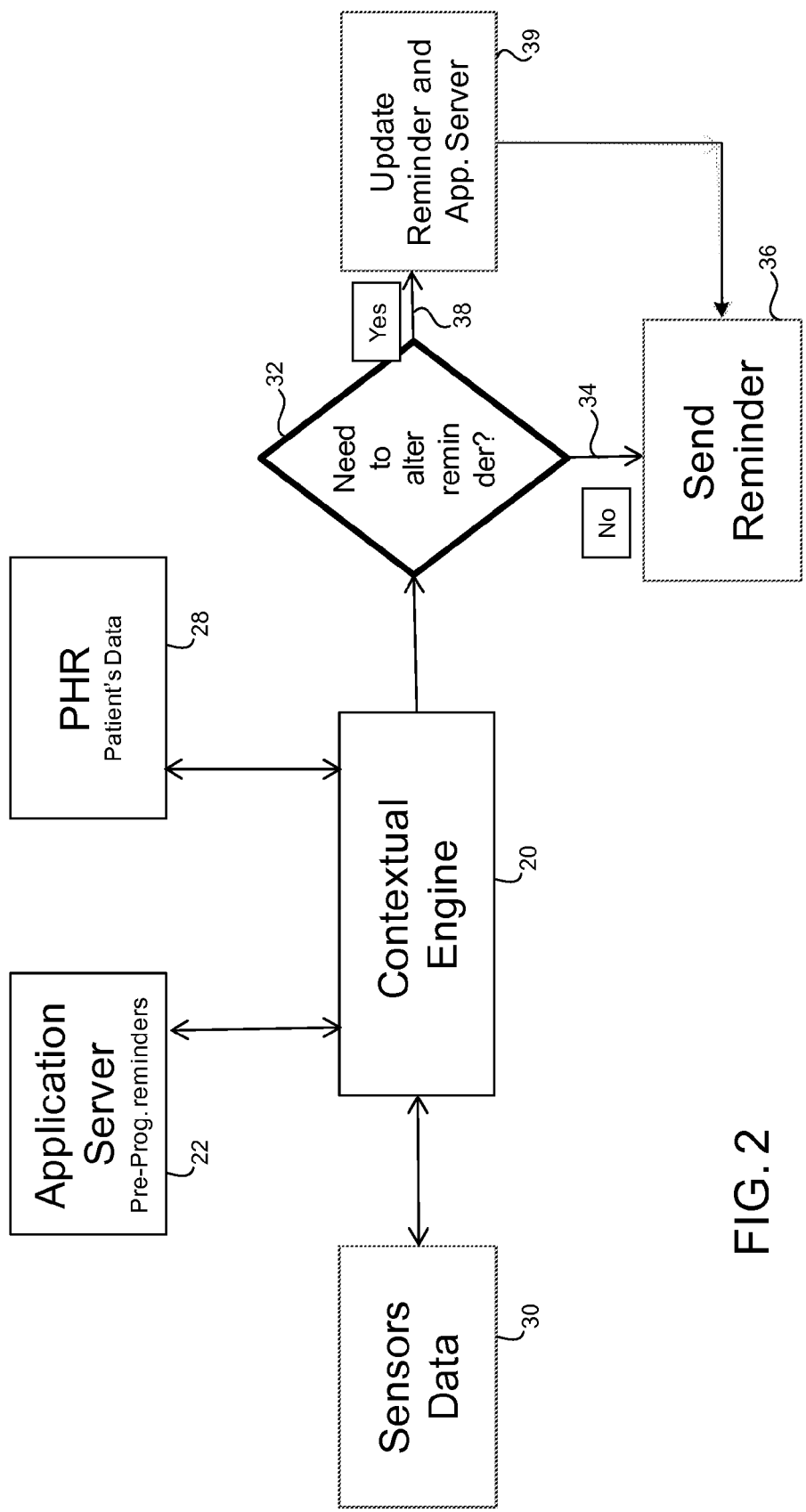
FIG. 2 is a schematic diagram of employment of a system for effecting context-cognizant reminders for a patient.

FIG. 2 is a schematic diagram of employment of a system for effecting context-cognizant reminders for a patient. In FIG. 2, sensor data 30 (received from sensor units $12_n$; FIG. 1) is provided to contextual engine 20 (see FIG. 1). Contextual engine 20 may also receive inputs from application server 22 (e.g., in the form of pre-programmed reminders) and from PHR 28 (e.g., in the form of data relating to a particular patient). The received information is evaluated by contextual engine 20 and a query is presented, represented by query block 32, whether there is a need to alter the reminder provided by application server 22.

If there is not a need to alter the reminder provided by application server 22, a decision is made according to NO response line 34 and a reminder is sent, as indicated by a block 36. If there is a need to alter the reminder provided by application server 22, a decision is made according to YES response line 36 and the reminder is updated (and application server 22 is updated) as indicated by a block 39. An updated reminder is then sent as indicated by block 36.

Figure 3:
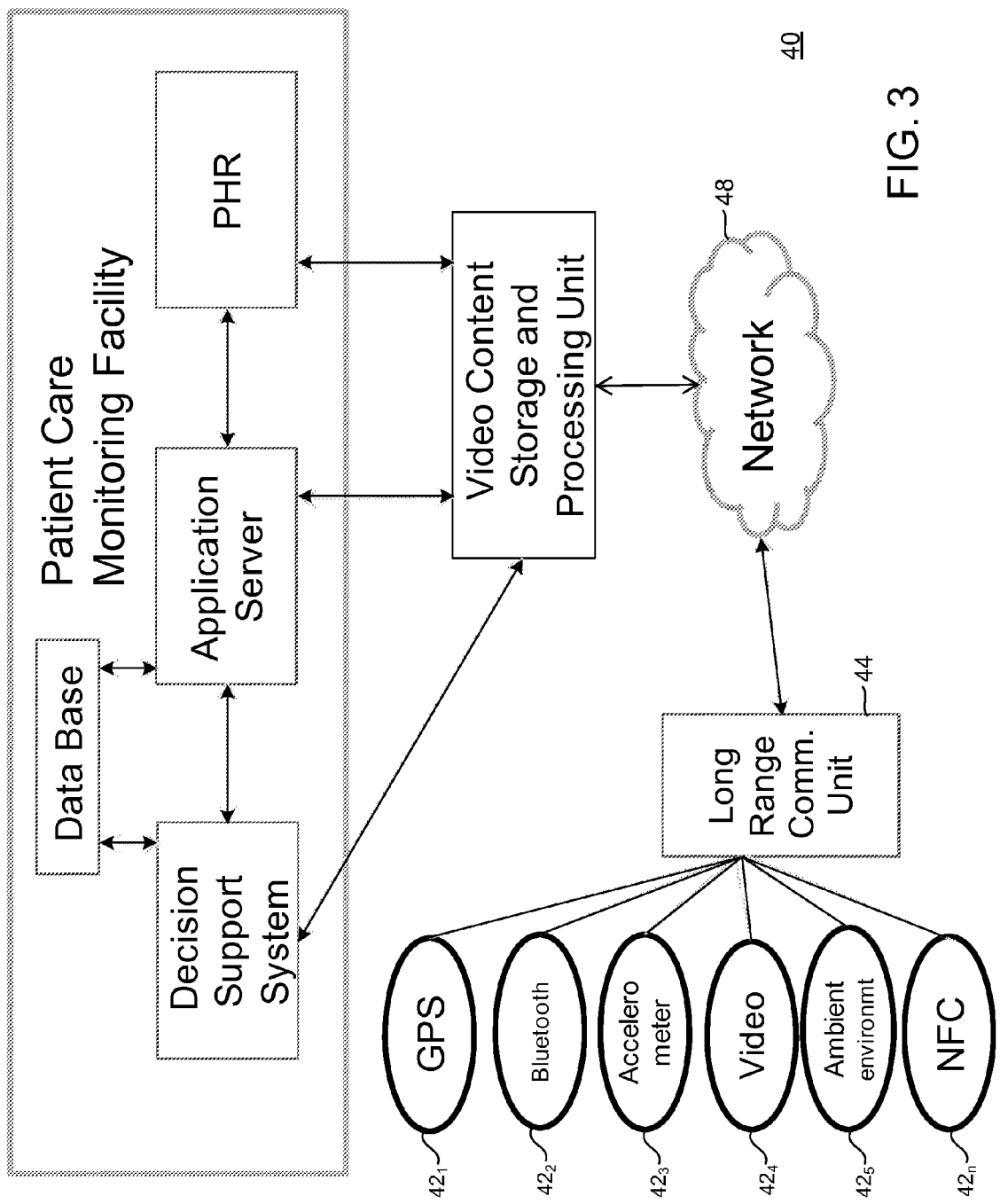
FIG. 3 is a schematic diagram of an alternate embodiment of a system for effecting context-cognizant reminders for a patient.

FIG. 3 is a schematic diagram of an alternate embodiment of a system for effecting context-cognizant reminders for a patient. In FIG. 3, a reminder system 40 includes a plurality of sensor units including a Global Positioning System position determining unit $42_1$, a Bluetooth or similar wireless linking unit $42_2$, an accelerometer unit $42_3$, a video unit $42_4$, an ambient environment measuring unit $42_5$ and a Near Field Communication (NFC) unit $42_m$.

The indicator "m" is employed to signify that there can be any number of sensor units in reminder system 40. The inclusion of six sensor units $42_1$, $42_2$, $42_3$, $42_4$, $42_5$ $42_m$ in FIG. 3 is illustrative only and does not constitute any limitation regarding the number of sensor units that may be included in the reminder system of the present invention. Throughout this description, use of a reference numeral using a generic subscript herein may be taken to mean that any respective member of the plurality of elements having the same reference numeral may be regarded as included in the description. Thus, by way of example and not by way of limitation, referring to sensor unit $42_m$ in describing FIG. 3 may be taken to mean that any sensor unit—Global Positioning System position determining unit $42_1$, Bluetooth or similar wireless linking unit $42_2$, accelerometer unit $42_3$, video unit $42_4$, ambient environment measuring unit $42_5$ or Near Field Communication (NFC) unit $42_m$ (FIG. 3) or another sensor unit not illustrated but understood by those skilled in the art of biometric measurement sensor devices—may be regarded as capable of employment as described.

Reminder system 40 also includes a long-range communication unit 44. Long-range communication unit 44 may be embodied in an intelligent wireless communication unit, such as by way of example and not by way of limitation, a smart phone or other smart device (such as a pendant). Long-range communication unit 44 is configured for wireless communication with a remote patient care monitoring facility 46 via a network 48.

Patient care monitoring facility 46 may include an application server 52 coupled with a database 54, with a decision support system 56 and with a Patient Health Record (PHR) 58. Preferably database 54 is also coupled with decision support system 56.

A video treating unit 50 may be coupled with patient care monitoring facility 56. Specifically, video treating unit 50 may be coupled with decision support system 56, application server 52 and PHR 58. Video treating unit 50, decision support system 56, application server 52 and PHR 58 may cooperate, with support from database 54, to interpret information provided by sensors $42_m$.

Cognitive Assistance

Patients may become lost or confused and may not recognize acquaintances because of memory loss, such as may occur with some mental diseases like Alzheimer's, Dementia or other diseases.

Prior art solutions involved placing a patient under direct supervision of a family member or other cognitively unimpaired person. Direct supervision is costly and deprives a patient of independence, freedom and privacy.

The present invention includes a combination of different technologies to assist patients to live a better and more productive, independent life style. Intelligent wireless communication units, such as smart phones or smart devices, employed in cooperation with a patient monitoring facility that may be embodied in a remote backend infrastructure and with smart combinatorial logic algorithms make assisting cognition in patients feasible.

Typical Alzheimer's warning signs may include:

Memory Loss that Disrupts Daily Life.

A patient may wear a smart phone or smart device around the neck as a pendant to record activities of the patient and be able to play back the recorded activities to aid in recollection of the activities. Activities may be recorded using a video camera. Triggering of a video camera and its shutter rate may be dependent on detection of activity by a smart device sensor. That is, a video camera could start recording in response to a voice or manual command or may automatically sense movement by an indication from an accelerometer combined with sensed GPS data. A Bluetooth or other wireless linking unit associated with the patient's unit may be paired with a linking unit of family members so that the smart phone may knows whether a patient is close to a family. Operation of a video camera, including shutter speed of the video camera, may be controlled according to the context or environment of a patient, including traveling speed of the patient.

Figure 4:
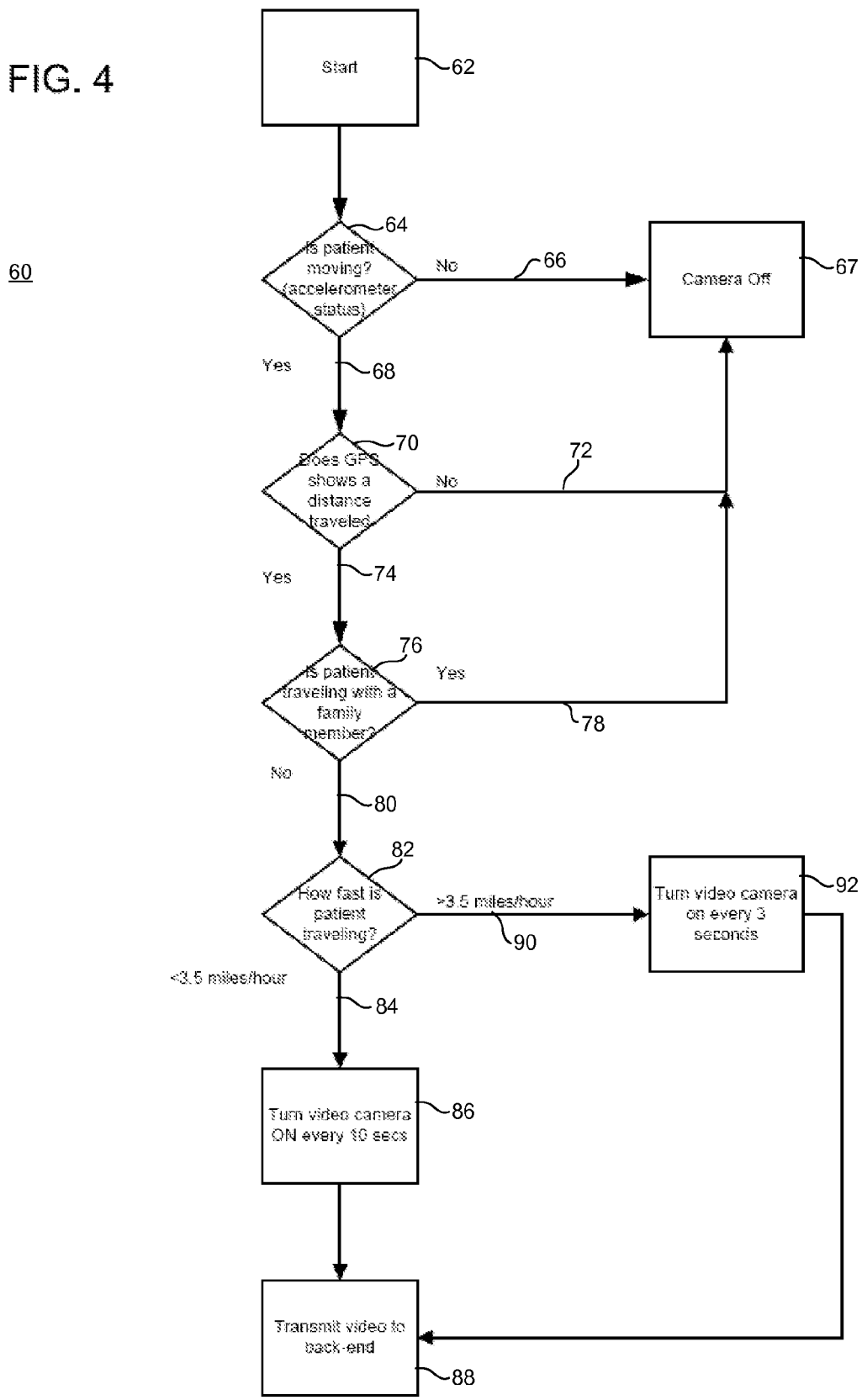
FIG. 4 is a schematic diagram of a first exemplary method for implementing a system for effecting cognitive assistance for a patient.

FIG. 4 is a schematic diagram of a first exemplary method for implementing a system for effecting cognitive assistance for a patient. In FIG. 4, a method 60 for effecting cognitive assistance for a patient begins at a START locus 62. Method 60 continues by posing a query whether the patient is moving (such information may be provided by a sensor unit such as an accelerometer; see FIGS. 1 and 3) as indicated by a query block 64. If the patient is not moving, method 60 proceeds from query block 64 via a NO response line 66 and the camera is turned off, as indicated by a block 67.

If the patient is moving, method 60 proceeds from block 64 via a YES response line 68 and another query is presented whether a GPS sensor shows a distance traveled, as indicated by a query block 70. If no distance is shown as having been traveled, method 60 proceeds from query block 70 via a NO response line 72 and the camera is turned off, as indicated by block 67.

If no distance is shown as having been traveled, method 60 proceeds from query block 70 via a NO response line 72 and the camera is turned off, as indicated by block 67. If some distance is shown as having been traveled, method 60 proceeds from query block 70 via a YES response line 74 and another query is presented whether the patient is traveling with a family member, as indicated by a query block 76. Whether the patient is traveling with a family member may be ascertained by an indication from a Bluetooth or similar wireless linking unit. If the patient is traveling with a family member, method 60 proceeds from query block 76 via a YES response line 78 and the camera is turned off, as indicated by block 67.

If the patient is not traveling with a family member, method 60 proceeds from query block 76 via a NO response line 80 and another query is posed whether the patient is traveling at a speed greater than a predetermined speed, as indicated by a query block 82. In the exemplary method 60 illustrated in FIG. 4, the predetermined speed is 3.5 miles per hour. If the patient is not traveling at a speed greater than the predetermined speed, method 60 proceeds from query block 82 via a "<[less than] predetermined speed" response line 84 and the video camera is turned on every 10 seconds. A typical walking speed for a person is approximately 3.0-3.5 miles per hour. This translates to approximately 7.4 seconds per 10 meters. It is for this reason that the shutter of the video camera is set to activate every 10 seconds. Method 60 thereafter transmits video data to patient monitoring facility that may be embodied in a remote backend infrastructure, as indicated by a block 88.

If the patient is traveling at a speed greater than the predetermined speed, method 60 proceeds from query block 82 via a ">[greater than] predetermined speed" response line 90 and the video camera is turned on every 3 seconds. Method 60 thereafter transmits video data to patient monitoring facility that may be embodied in a remote backend infrastructure, as indicated by block 88.

Challenges in Following a Plan or Working with Numbers.

A plan may be entered in advance into a smart device and may be made easily accessible by a patient. The calculator features of the smart phone may assist in dealing with numbers.

Difficulty Completing Familiar Tasks.

Tasks may be pre-recorded in a smart phone correctly and when a patient is doing the tasks by himself, then a current video recording may be compared with the pre-recorded one at a patient monitoring facility. The patient monitoring facility may exercise software to identify task steps and highlight differences between currently performed task steps and pre-recorded task steps to the user. Alternatively, a next task step may be displayed for a patient when the patient stalls.

Figure 5:
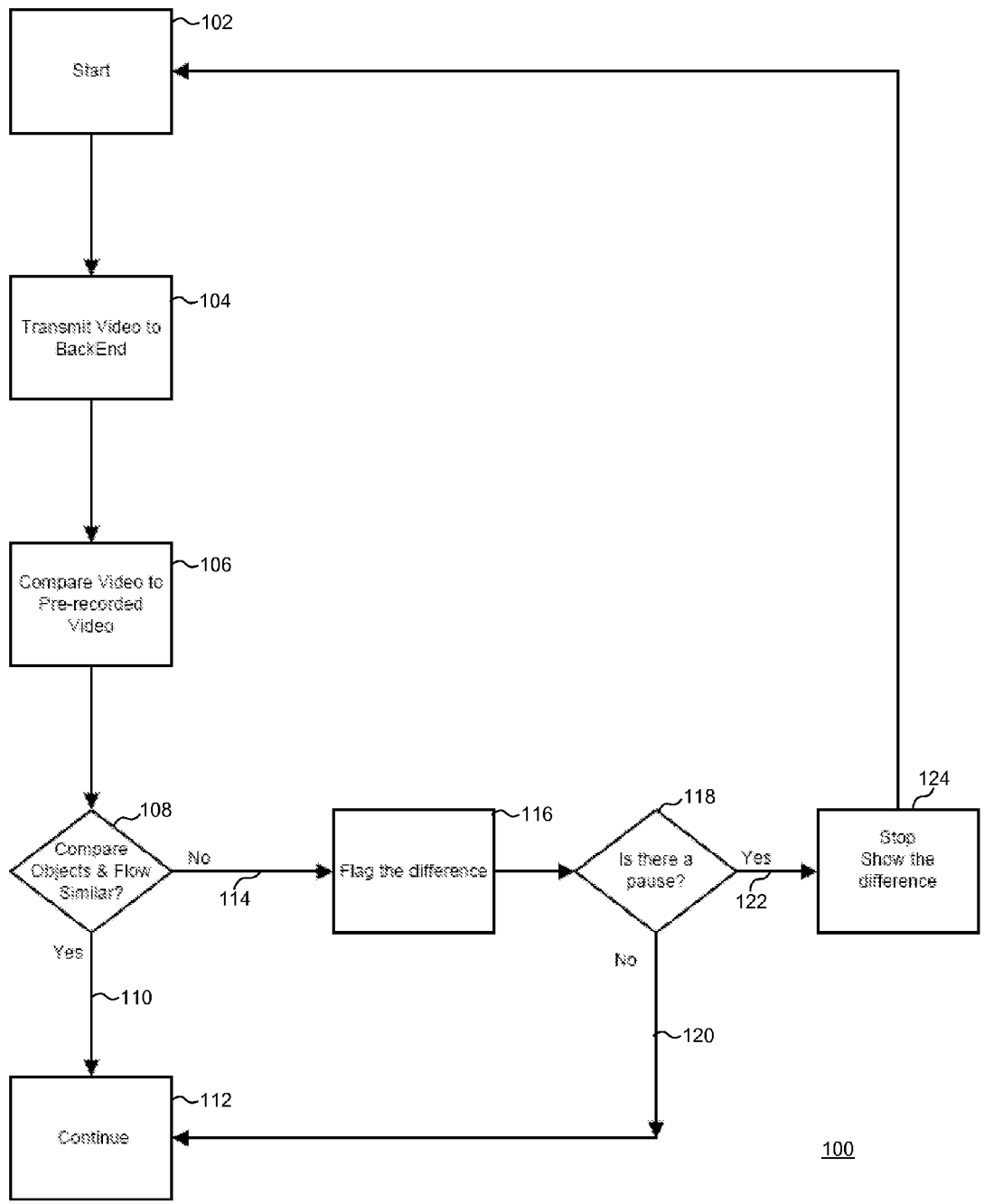
FIG. 5 is a schematic diagram of a second exemplary method for implementing a system for effecting cognitive assistance for a patient.

FIG. 5 is a schematic diagram of a second exemplary method for implementing a system for effecting cognitive assistance for a patient. In FIG. 5, a method for implementing a system for effecting cognitive assistance 100 begins at a START locus 102. Method 100 continues with transmitting video data to a patient monitoring facility that may be embodied in a remote backend infrastructure, as indicated by block 104.

Method 100 continues with comparing the transmitted video data with pre-recorded video data, as indicated by a block 106.

Method 100 continues with posing a query whether the compared video data are similar, as indicated by a query block 108. If the compared video data are similar, method 100 proceeds from query block 108 via a YES response line 110 and method 100 continues, returning to START locus 102 as indicated by block 112 (return to START locus 102 not shown in FIG. 5).

If the compared video data are not similar, method 100 proceeds from query block 108 via a NO response line 114 and the difference(s) are flagged for review, as indicated by a block 116.

Method 100 continues with posing a query whether the patient has exhibited a pause in the transmitted video data, as indicated by a query block 118. If there is no pause in the transmitted video data, method 100 proceeds from query block 118 via a NO response line 120 and method 100 continues, returning to START locus 102 as indicated by block 112 (return to START locus 102 not shown in FIG. 5).

If there is no pause in the transmitted video data, method 100 proceeds from query block 118 via a YES response line 122 and method 100 stops video transmissions to exhibit the difference between the transmitted video data and the pre-recorded video data, as indicated by a block 124. Method 100 continues from block 124 by returning to START locus 102.

Confusion with Time and Place.

A clock in a smart phone may assist in overcoming time confusion and pre-recorded pictures may identify places.

Trouble Understanding Visual Images and Spatial Relationships.

A patient may take a picture of the visual images with which he is having problems, and the pictures taken may be compared with stored pictures in a patient monitoring facility for identification. Similarly, if a patient is having problems with judging distances, he can enter an estimated distance in a smart phone which in turn may compare the location of the patient (determined, for example, using GPS) with respect to the estimated distanced provided by the patient.

New Problems with Words in Speaking or Writing.

A smart phone can record and analyze an audio recording of a patient's conversation and may be able to make suggestions when the patient stops in the middle of a conversation without an apparent idea on how to continue. Alternatively, if a patient repeats himself an indicator may flash or a honk sound may be presented.

Figure 6:
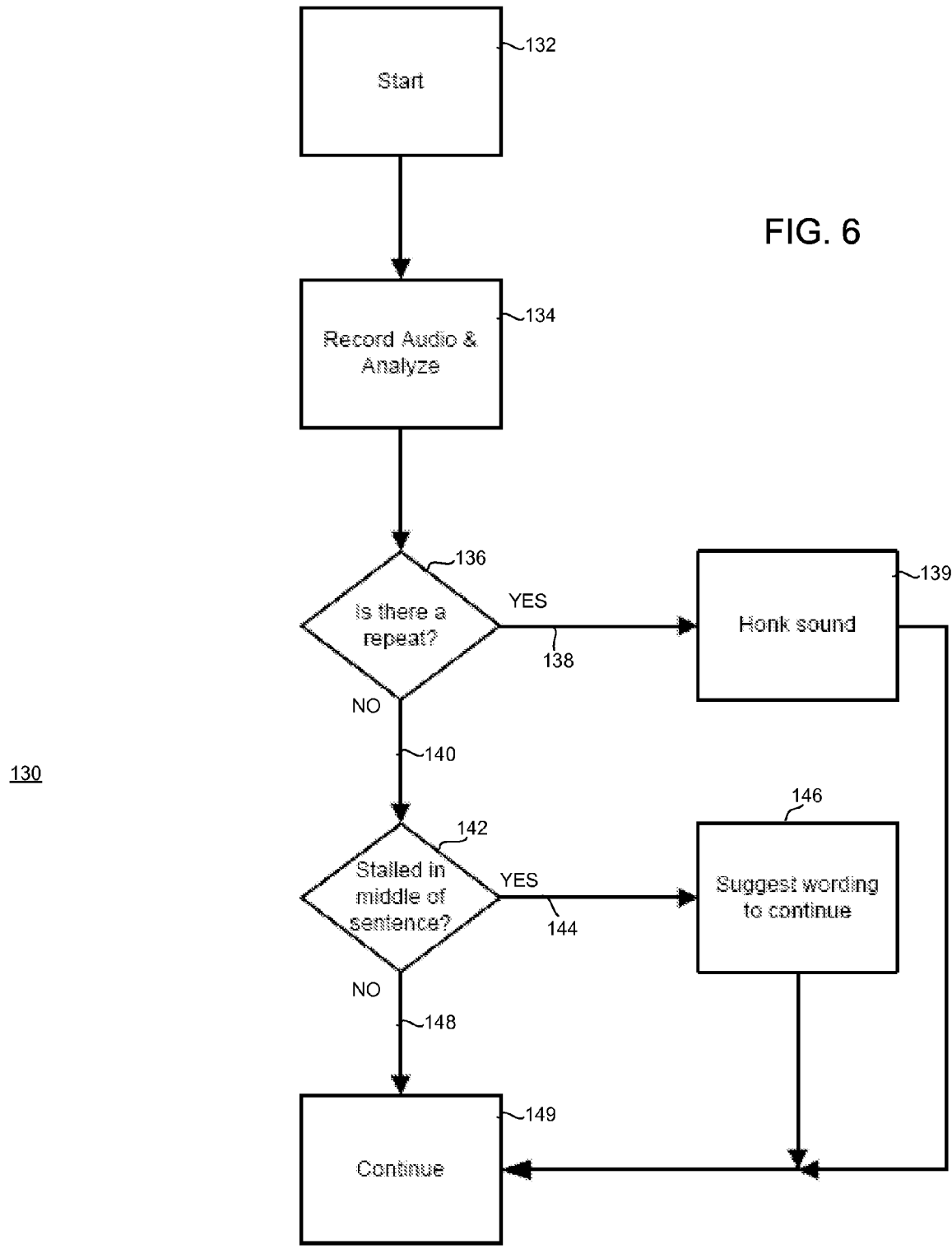
FIG. 6 is a schematic diagram of a third exemplary method for implementing a system for effecting cognitive assistance for a patient.

FIG. 6 is a schematic diagram of a third exemplary method for implementing a system for effecting cognitive assistance for a patient. In FIG. 6, a method for implementing a system for effecting cognitive assistance for a patient 130 begins at a START locus 132. Method 130 continues with recording and analyzing speech of the patient, as indicated by a block 134.

Method 130 continues with posing a query whether the patent has repeated himself, as indicated by a query block 136. If the patient has repeated himself, method 130 proceeds from query block 136 via a YES response line 138 and an alarm is sounded, such as a honk, as indicated by a block 139. Method 130 continues, returning to START locus 132 as indicated by block 149 (return to START locus 132 not shown in FIG. 6).

If the patient has not repeated himself, method 130 proceeds from query block 136 via a NO response line 140 and poses a query whether the patient has stalled in the middle of a sentence, as indicated by a query block 142. If the patient has stalled in the middle of a sentence, method 130 proceeds from query block 142 via a YES response line 144 and wording is suggested to the patient in order to continue, as indicated by a block 146. Method 130 continues, returning to START locus 132 as indicated by block 149 (return to START locus 132 not shown in FIG. 6).

If the patient has not stalled in the middle of a sentence, method 130 proceeds from query block 142 via a NO response line 148. Method 130 continues, returning to START locus 132 as indicated by block 149 (return to START locus 132 not shown in FIG. 6).

Misplacing Things and Losing the Ability to Retrace Steps.

A patient may employ Bluetooth tags (or similar wireless identification devices) on items that tend to get misplaced. A patient monitoring facility may employ resources such as software programming to keep track of the last place where the tag was detected. The misplaced object location may be detected using a combination of Bluetooth indoor and GPS outdoor location determination.

Decreased or Poor Judgment.

Poor judgment when dealing with money may be pointed out using a Near Field Communication (NFC) device on a smart phone. NFC is a short-range communication technology which enables the exchange of data between devices over a few inches distances, and it is intended for secure payments. A patient monitoring facility may download an application on a patient's smart phone that would require the authorization of a family member before the patient's could go through a monetary or other transaction. Alternatively, this feature could be enabled depending upon whether the transaction amount is above a predetermined amount.

Withdrawal from Work or Social Activities

A smart phone can identify a family member if the patient is not traveling or interacting with others as may be determined by monitoring a Bluetooth tag worn by the family member and by monitoring conversations around the patient.

Changes in Mood and Personality

When a patient starts to become confused, suspicious, depressed, fearful or anxious, he can be reassured and entertained by smart phone applications, videos or music. The smart phone may access happy events stored in the patient monitoring facility.

Mobile remote monitoring programs are not presently reimbursed by the health insurance companies, but video monitoring and consultation may be reimbursed. In the past, using prior art technology, remote video monitoring required expensive and bulky equipment. The prior art equipment was too bulky for convenience and too costly for health insurance companies to provide reimbursement.

The present invention leverages the two way video capability of intelligent wireless communication units, such as smart phones or smart devices, by automatically establishing a video link with a caregiver when a script identifies a need for video monitoring or consultation.

Figure 7A:
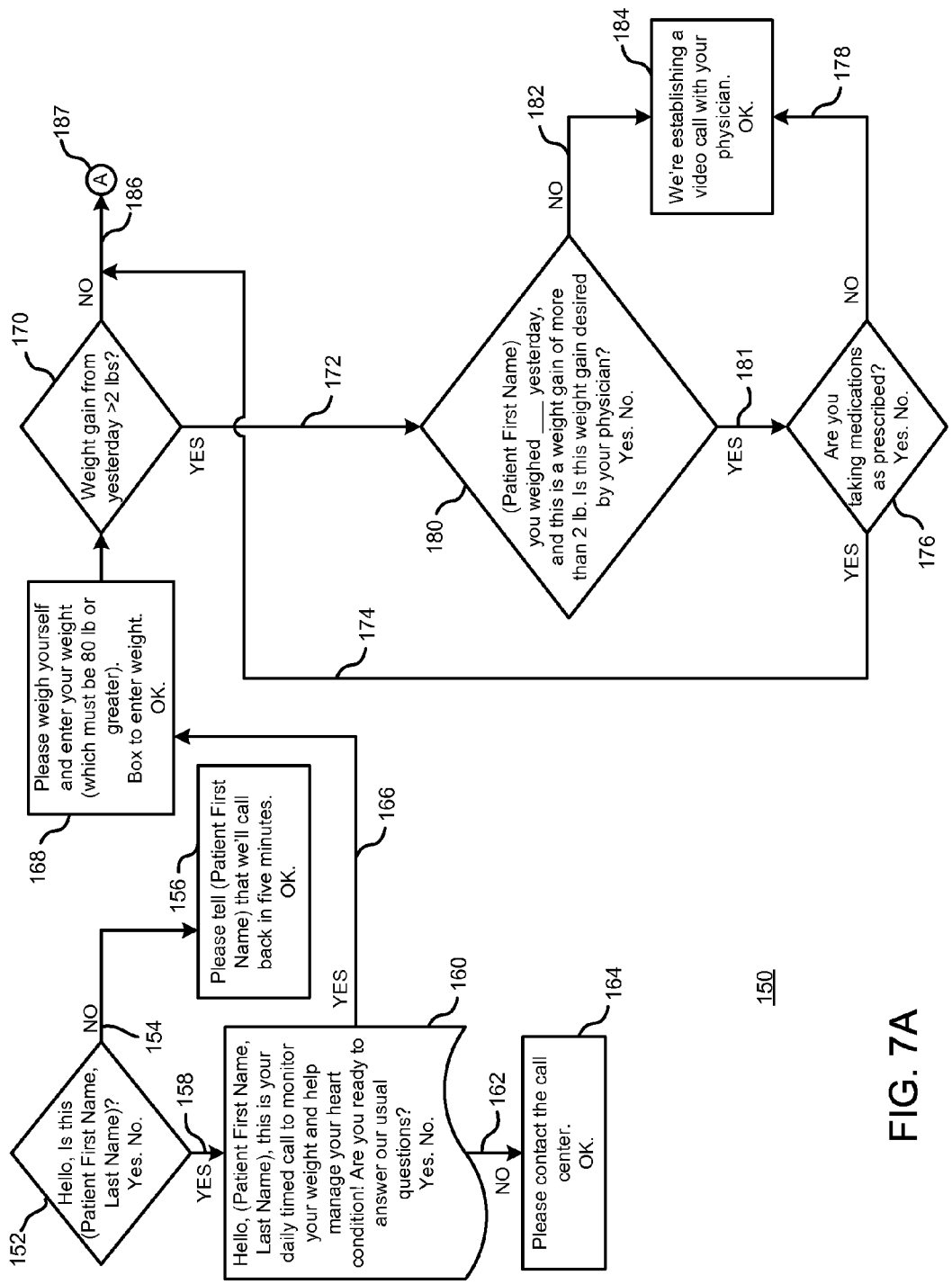
FIG. 7A and &B present a flow diagram illustrating a first exemplary on-line medical consultation.

FIGS. 7A and &B present a flow diagram illustrating a first exemplary on-line medical consultation. In FIG. 7A, a method for on-line medical consultation 150 begins with posing a query "Hello. Is this [Patient First Name, Patient Last Name]?" as indicated by a block 152. If the patient answers "No", method 150 proceeds via a NO response line 154 and presents an announcement, "Please tell [Patient First Name, Patient Last Name] we'll call back in five minutes," as indicated by a block 154. If the patient responds "Yes" method 150 proceeds via a YES response line 158 and states, "Hello, [Patient First Name]. This is your daily timed call to monitor your weight and help manage your heart condition! Are you ready to answer our usual questions?" as indicated by a block 160.

If the patient answers "No" method 150 proceeds via a NO response line 162 and presents an announcement, "Please contact the call center" as indicated by a block 164. If the patient responds "Yes" method 150 proceeds via a YES response line 166 and states "Please weigh yourself and enter your weight (which must be 80 lb or greater)" and displays a box in which the patient may enter his weight as indicated by a block 168.

Method 150 next presents a query whether the patient's weight gain from yesterday is greater than 2 pounds, as indicated by a query block 170. If the patient responds "Yes", method 150 proceeds via a YES response line 172 and method 150 next poses a query, "[Patient First Name], you weighed_____yesterday, and this is a weight gain of more than 2 lbs. Is this weight gain desired by your physician?" as indicated by a query block 180. If the patient responds "Yes", method 150 proceeds from query block 180 via a YES response line 181 to pose a query, "Are you taking medications as prescribed?" as indicated by a query block 176.

If the patient responds to the query posed by either query block 176 or query block 180 with "No", method 150 announces to the patient, "We're establishing a video call with your physician" as indicated by a block 184.

If the patient responds to the query posed by query block 176 with "Yes", method 150 proceeds via YES response line 174.

Figure 7B:
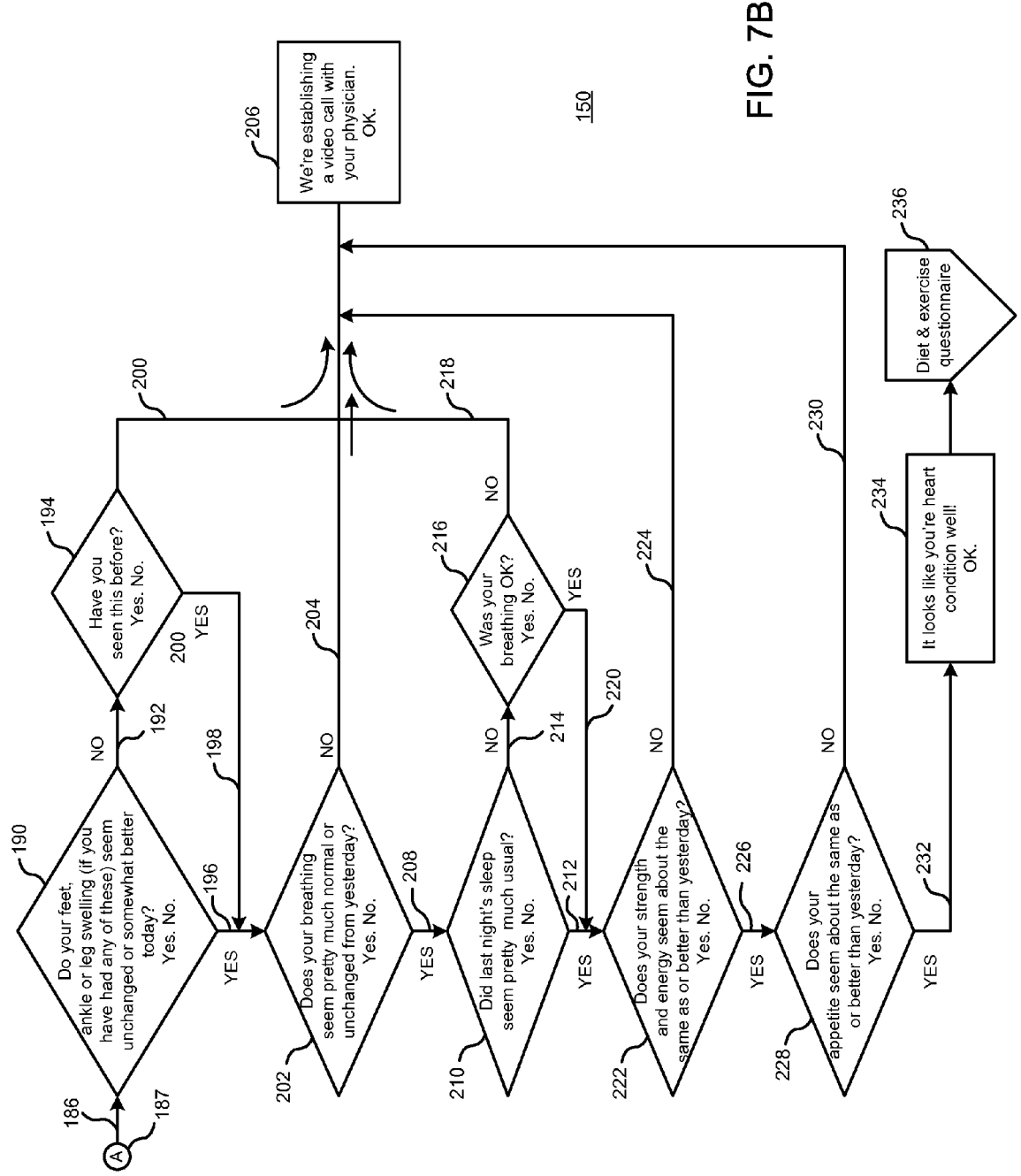

If the patient responds to the query posed by query block 170 with "No" or responds "Yes" to the query posed by query block 176, method 150 proceedss via a line 186 and connector "A" 187 to FIG.7B and poses a query, "Do your feet, ankle, or leg swelling (if you have had any of these) seem unchanged or somewhat better today?" as indicated by a query block 190. If the patient responds "Yes", method 150 proceeds from query block 190 via a YES response line 196 to pose a query, "Does your breathing seem pretty much normal or unchanged from yesterday?" as indicated by a query block 202.

If the patient responds "No" to the query posed by query block 190, method 150 proceeds from query block 190 via a NO response line 192 to pose a query, "Have you seen this before?" as indicated by a query block 194. If the patient responds "No" to the query posed by query block 194, method 150 proceeds from query block 190 via a NO response line 200 to a block 206 at which an announcement is presented to the patient, "We're establishing a video call with your physician."

If the patient responds "Yes" to the query posed by query block 194, method 150 proceeds from query block 190 via a YES response line 198 to query block 202.

Query block 202 poses a query, "Does your breathing seem pretty much normal or unchanged from yesterday?" If the patient responds "No" to the query posed by query block 202, method 150 proceeds from query block 202 via a NO response line 204 block 206 at which an announcement is presented to the patient, "We're establishing a video call with your physician." If the patient responds "Yes" to the query posed by query block 202, method 150 proceeds from query block 202 via a YES response line 208 to a query block 210.

Query block 210 poses a query, "Did last night's sleep seem pretty much usual?" If the patient responds "Yes" to the query posed by query block 210, method 150 proceeds from query block 210 via a YES response line 212 to a query block 222. If the patient responds "No" to the query posed by query block 210, method 150 proceeds from query block 210 via a NO response line 214 to pose a query, "Was your breathing ok?" as indicated by a query block 216. If the patient responds "No" to the query posed by query block 216, method 150 proceeds from query block 216 via a NO response line 218 to block 206 at which an announcement is presented to the patient, "We're establishing a video call with your physician."

If the patient responds "Yes" to the query posed by query block 216, method 150 proceeds from query block 216 via a YES response line 220 to query block 222.

Query block 222 poses a query, "Does your strength and energy seem about the same as or better than yesterday?" If the patient responds "Yes" to the query posed by query block 222, method 150 proceeds from query block 222 via a YES response line 226 to a query block 228. If the patient responds "No" to the query posed by query block 222, method 150 proceeds from query block 222 via a NO response line 224 to block 206 at which an announcement is presented to the patient, "We're establishing a video call with your physician."

Query block 228 poses a query, "Does your appetite seem pretty much the same as or better than yesterday?" If the patient responds "Yes" to the query posed by query block 228, method 150 proceeds from query block 228 via a YES response line 232 to a block 234. If the patient responds "No" to the query posed by query block 228, method 150 proceeds from query block 228 via a NO response line 230 to block 206 at which an announcement is presented to the patient, "We're establishing a video call with your physician."

Block 234 presents a congratulatory statement, "It looks like you're managing your heart condition well!" Method thereafter may pass the patient to a diet and exercise questionnaire (FIG. 8), as indicated by a block 236.

Figure 8:
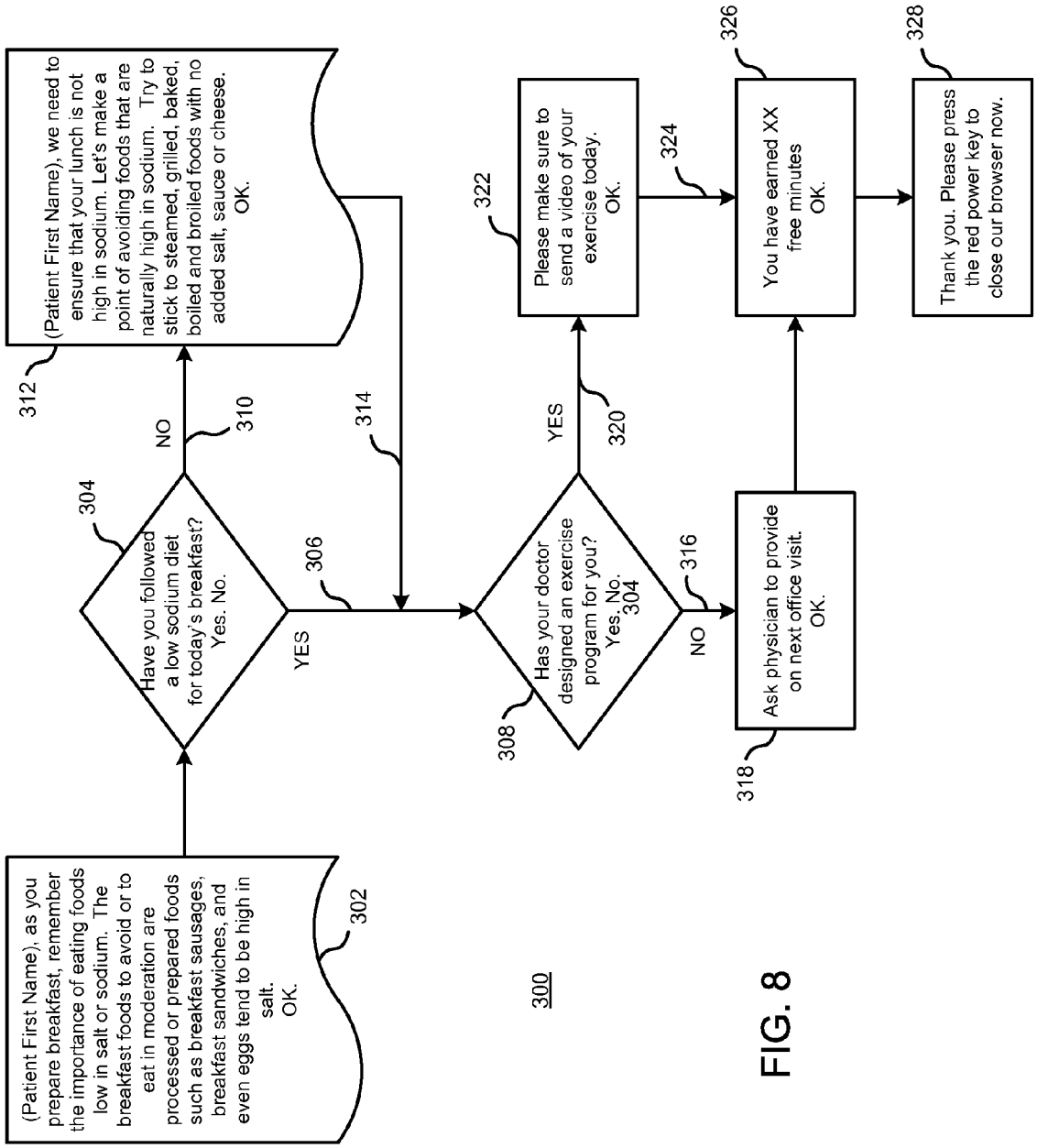
FIG. 8 is a flow diagram illustrating a second exemplary on-line medical consultation.

FIG. 8 is a flow diagram illustrating a second exemplary on-line medical consultation. In FIG. 8, a method 300 for dietary and exercise consultation begins with a morning greeting, "[Patient First Name], as you prepare breakfast, remember the importance of eating foods low in salt or sodium. The breakfast foods to avoid or to eat in moderation are processed or prepared foods such as breakfast sausages, breakfast sandwiches, and even eggs tend to be high in salt" as indicated by a block 302. Method 300 continues with posing a query, "Have you followed a low sodium diet for today's breakfast?" as indicated by a query block 304. If the patient responds "Yes", method 300 proceeds from query block 304 via a YES response line 306 to pose a query, "Has your doctor designed an exercise program for you?" as indicated by a query block 308.

If the patient responds "No" to the query posed by query box 304, method 300 proceeds from query box 304 via a NO response line 310 and a comment is presented to the patient, "[Patient First Name], we need to ensure that your lunch is not high in sodium. Let's make a point of avoiding foods that are naturally high in sodium. Try to stick to steamed, grilled, baked, boiled, and broiled foods with no added salt, sauce, or cheese." As indicated by a block 312. Method 300 proceeds from block 312 via a line 314 to query block 308.

Query block 308 poses a query, "Has your doctor designed an exercise program for you?" If the patient responds "No" to the query posed by query block 308, method 300 proceeds from query block 308 via a NO response line 316 and presents a request to the patient, "Ask physician to provide on next office visit" as indicated by a block 318. If the patient responds "Yes" to the query posed by query block 308, method 300 proceeds from query block 308 via a YES response line 320 to present a request to the patient, "Please make sure to send a video of your exercise today" as indicated by a block 322.

Method 300 proceeds from either of block 318 or block 322 to a block 326 at which the patient is advised, "You have earned xx free minutes."

Method 300 proceeds from block 326 to a block 328 at which the patient is advised, "Thank you. Please press the red power key to close your browser now." Method 300 is thereby terminated.

Using prior art technology, a patient obtained vital signs and other biometric measurements manually or via a Bluetooth connection (or a similar wireless linking arrangement). The prior art technology also required a patient to remember or to be reminded to measure his biometric data.

The present invention permits automatic loading of a patient's biometric data into a patient monitoring facility that may be embodied in a remote backend infrastructure for continuous monitoring of vital and biometrical signs. A need for reminders may be eliminated.

Subcutaneous devices for blood pressure or glucose measurements may be positioned in areas where sensor receptors on the patient's clothing can pick-up weak signals typically generated by such subcutaneous sensors and retransmit the weak signals through a body area network and into an intelligent wireless communication unit, such as a smart phone or a smart device. The smart phone may subsequently automatically retransmit the sensor signal to a patient monitoring facility that may be embodied in a remote backend infrastructure.

By way of example and not by way of limitation, for CHF (Congestive Heart Failure) special shoes with weight sensors may relay a patient's weight automatically to a patient monitoring facility that may be embodied in a remote backend infrastructure.

Figure 9:
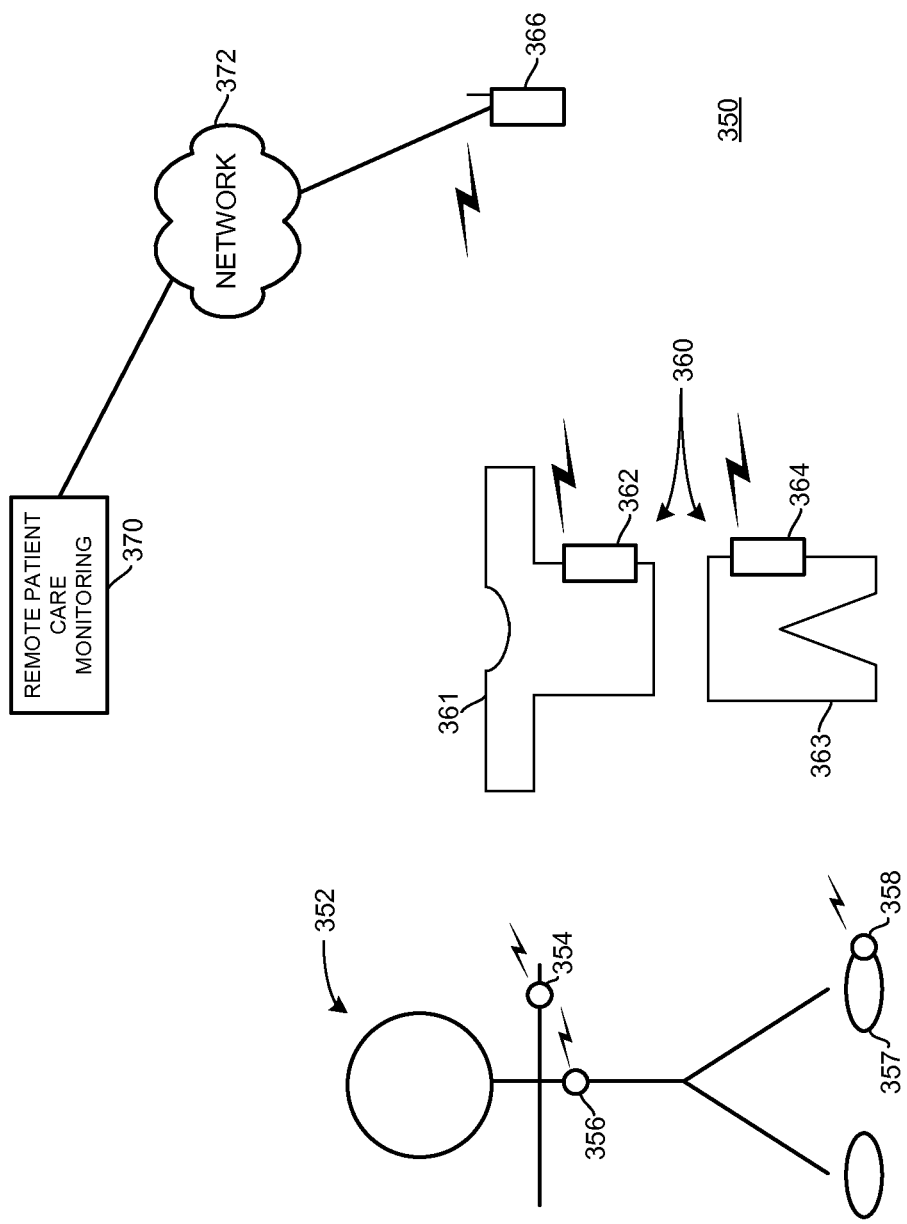
FIG. 9 is a schematic diagram illustrating employment of wearable or otherwise patient-carried biometric data measuring devices.

FIG. 9 is a schematic diagram illustrating employment of wearable or otherwise patient-carried biometric data measuring devices. In FIG. 9, a remote biometric measuring system 350 is provided for a patient 352. Remote biometric measuring system 350 may include a plurality of wearable sensors 354, 356, 358. One or more wearable sensor 354, 356 may be subcutaneously worn by patient 352. Sensor 358 may be embodied in a weight-sensing unit incorporated within a shoe 357 worn by patient 352.

Sensors 354, 356, 358 are configured for wirelessly communicating data relating to a respective parameter being sensed by each of sensors 354, 356, 358. Some sensors, such as by way of example and not by way of limitation subcutaneous sensors, may be incapable of presenting more than a somewhat weak communication signal able to travel only a limited distance. When such weak-transmitting sensors are employed in remote biometric measuring system 350 a body area network 360 may be provided. Body area network 360 may include a plurality of repeater units 362, 364. Repeater units 362, 364 receive signals from selected (weak-transmitting) sensors 354, 356, 358 and retransmit the data in the signals to a long-range communication unit 366. Repeater units 362, 364 may be sewn into clothing such as a shirt 361 or trousers 363 or other clothing items (not shown in FIG. 9). Repeater units 362, 364 may be carried in pockets of clothing 361, 363 otherwise associated with clothing 361, 363 or other clothing items to permit repeater units 362, 364 accompanying patient 352.

Long range communication unit 366 may be embodied in a smart phone, a smart pendant or another long-range communication unit configured for wireless communicating with a remote patient care monitoring facility 370 via a wireless communication network 372 or other network.

It is to be understood that, while the detailed drawings and specific examples given describe preferred embodiments of the invention, they are for the purpose of illustration only, that the apparatus and method of the invention are not limited to the precise details and conditions disclosed and that various changes may be made therein without departing from the spirit of the invention which is defined by the following claims:

We claim:

1. A system for effecting context-cognizant cognitive assistance for a patient; the system comprising:
   (a) at least one sensor unit attached with said patient selected from the group consisting of: a video sensor and an audio sensor;

(b) at least one long-range communication unit configured for wireless communication with a remote patient care monitoring facility via a wireless communication network and configured to receive sensor data from the sensor unit;

(c) a remote backend system at the patient care monitoring facility configured to provide cognitive assistance to the patient via the long-range communication unit based on the sensor data; and, (d) a motion sensor selected from the group consisting of a Global Positioning System position determining unit (GPS) and an accelerometer, wherein the backend system is configured to command the sensor to collect video data if the motion sensor indicates that the patient is in motion.

2. A system for effecting context-cognizant cognitive assistance for a patient; the system comprising:

(a) at least one sensor unit attached with said patient selected from the group consisting of: a video sensor and an audio sensor;

(b) at least one long-range communication unit configured for wireless communication with a remote patient care monitoring facility via a wireless communication network and configured to receive sensor data from the sensor unit; and (c) a remote backend system at the patient care monitoring facility configured to provide cognitive assistance to the patient via the long-range communication unit based on the sensor data; and (d) a short range communications unit configured to detect an electronic tag worn by a cognitively unimpaired person supervising the patient;

wherein the backend system is configured to command the sensor to collect video data depending on whether the caretaker is proximate to the patient.

3. A system for effecting context-cognizant cognitive assistance for a patient; the system comprising:

(a) at least one sensor unit attached with said patient selected from the group consisting of: a video sensor and an audio sensor;

(b) at least one long-range communication unit configured for wireless communication with a remote patient care monitoring facility via a wireless communication network and configured to receive sensor data from the sensor unit; and (c) a remote backend system at the patient care monitoring facility configured to provide cognitive assistance to the patient via the long-range communication unit based on the sensor data, wherein the backend system is configured to receive a request from the patient for assistance in completing a task, and to transmit video instruction relating to the completion of a task to the patient.

* * * * *